United States Patent
DiFiore

(10) Patent No.: US 10,525,192 B2
(45) Date of Patent: Jan. 7, 2020

(54) INSERT FOR CATHETER SYSTEM

(71) Applicant: ATTWILL MEDICAL SOLUTIONS STERILFLOW L.P., Salt Lake City, UT (US)

(72) Inventor: Attilio DiFiore, West Jordan, UT (US)

(73) Assignee: Attwill Medical Solutions Steriflow L.P., Salt Lake City, UT (US)

( * ) Notice: Subject to any disclaimer, the term of this patent is extended or adjusted under 35 U.S.C. 154(b) by 0 days.

(21) Appl. No.: 15/312,995

(22) PCT Filed: May 20, 2015

(86) PCT No.: PCT/US2015/031818
§ 371 (c)(1),
(2) Date: Nov. 21, 2016

(87) PCT Pub. No.: WO2015/179548
PCT Pub. Date: Nov. 26, 2015

(65) Prior Publication Data
US 2017/0182241 A1  Jun. 29, 2017

Related U.S. Application Data

(60) Provisional application No. 62/001,487, filed on May 21, 2014.

(51) Int. Cl.
*A61M 5/14* (2006.01)
*A61M 25/00* (2006.01)
(Continued)

(52) U.S. Cl.
CPC ............ *A61M 5/14* (2013.01); *A61M 5/2448* (2013.01); *A61M 5/31596* (2013.01);
(Continued)

(58) Field of Classification Search
CPC .... A61M 25/00; A61M 25/0097; A61M 5/14; A61M 25/01; A61M 39/16;
(Continued)

(56) References Cited

U.S. PATENT DOCUMENTS 4,533,348 A   8/1985  Wolfe et al.
4,874,366 A   10/1989 Zdeb et al.
(Continued)

FOREIGN PATENT DOCUMENTS

CA   1173795 A   9/1984
EP   0353018 A1  1/1990
(Continued)

OTHER PUBLICATIONS

De Cock et al.; "Topical Heparin in the Treatment of Ligneous Conjunctivitis"; Ophthalmology; (Oct. 31, 1995); pp. 1654-1659; vol. 102, No. 11; <doi: pubmed: 9098258 >.
(Continued)

*Primary Examiner* — Theodore J Stigell
(74) *Attorney, Agent, or Firm* — Thorpe North & Western LLP

(57) ABSTRACT

An insert for a catheter system can include an insert housing which defines a portion of a fluid pathway of the catheter system, a cartridge positioned within the insert housing in a manner to allow fluid flow along the fluid pathway such that fluid contacts the insert during the fluid flow, and an active agent associated with the cartridge. The active agent and the cartridge can be adapted to release active agent from the cartridge during the fluid flow.

19 Claims, 9 Drawing Sheets

(51) Int. Cl.
*A61M 25/01* (2006.01)
*A61M 39/16* (2006.01)
*A61M 5/24* (2006.01)
*A61M 5/315* (2006.01)

(52) U.S. Cl.
CPC ........ *A61M 25/00* (2013.01); *A61M 25/0097* (2013.01); *A61M 25/01* (2013.01); *A61M 39/16* (2013.01); *A61M 39/162* (2013.01); *A61M 2025/0019* (2013.01); *A61M 2025/0056* (2013.01); *A61M 2025/0057* (2013.01)

(58) Field of Classification Search
CPC .............. A61M 5/2448; A61M 39/162; A61M 5/31596; A61M 2025/0057; A61M 2025/0056; A61M 2025/0019
See application file for complete search history.

(56) References Cited

U.S. PATENT DOCUMENTS

| | | | |
|---|---|---|---|
| 4,963,132 | A | 10/1990 | Gibson |
| 5,006,114 | A | 4/1991 | Rogers et al. |
| 5,024,657 | A | 6/1991 | Needham et al. |
| 5,030,203 | A | 7/1991 | Wolf, Jr. et al. |
| 5,049,139 | A | 9/1991 | Gilchrist |
| 5,098,394 | A | 3/1992 | Luther |
| 5,205,820 | A | 4/1993 | Kriesel |
| 5,395,323 | A | 3/1995 | Berglund |
| 5,547,471 | A | 8/1996 | Thompson et al. |
| 5,984,373 | A | 11/1999 | Fitoussi et al. |
| 6,105,442 | A | 8/2000 | Kriesel et al. |
| 6,406,879 | B2 | 6/2002 | James et al. |
| 6,702,850 | B1 | 3/2004 | Byun et al. |
| 6,805,685 | B2 | 10/2004 | Taylor |
| 7,045,585 | B2 | 5/2006 | Berry et al. |
| 7,081,109 | B2 | 7/2006 | Tighe et al. |
| 2003/0124705 | A1 | 7/2003 | Berry et al. |
| 2005/0124970 | A1 | 6/2005 | Kunin |
| 2007/0003603 | A1 | 1/2007 | Karandikar |
| 2007/0042015 | A1 | 2/2007 | Berry et al. |
| 2008/0027401 | A1 | 1/2008 | Ou-Yang |
| 2008/0097407 | A1 | 4/2008 | Plishka |
| 2008/0140055 | A1 | 6/2008 | Shirley |
| 2009/0163876 | A1 | 6/2009 | Chebator et al. |
| 2009/0281059 | A1 | 11/2009 | Falotico et al. |
| 2010/0198148 | A1 | 8/2010 | Zinger et al. |
| 2011/0054440 | A1* | 3/2011 | Lewis ............... A61M 39/16 604/506 |
| 2011/0066120 | A1 | 3/2011 | Lee |
| 2011/0257606 | A1 | 10/2011 | Truitt et al. |
| 2012/0083750 | A1 | 4/2012 | Sansoucy |
| 2013/0085474 | A1 | 4/2013 | Charles et al. |
| 2013/0172853 | A1 | 7/2013 | McClain et al. |
| 2013/0338644 | A1 | 12/2013 | Solomon et al. |
| 2015/0306367 | A1 | 10/2015 | DiFiore |

FOREIGN PATENT DOCUMENTS

| | | |
|---|---|---|
| EP | 1663299 A2 | 6/2006 |
| GB | 2187388 A | 9/1987 |
| JP | S60-138544 U | 9/1985 |
| WO | WO 86/03416 | 6/1986 |
| WO | WO 94/22522 | 10/1994 |
| WO | WO 2002/005873 | 1/2002 |
| WO | WO 2008/014440 | 1/2008 |
| WO | WO 2013/023146 | 2/2013 |
| WO | WO 2013023146 A1 * | 2/2013 |
| WO | WO 2013/110956 A1 | 8/2013 |
| WO | WO 2015/109162 A1 | 7/2015 |

OTHER PUBLICATIONS

Fine et al.; "Successful Treatment of Ligneous Gingivitis with Warfarin"; Oral Surgery, Oral Medicine, Oral Pathology, Oral Radiology; (Jan. 1, 2009); pp. 77-80; vol. 107, No. 1; <doi: 10.1016/j.tripleo.2008.08.007 >.

* cited by examiner

INSERT FOR CATHETER SYSTEM

BACKGROUND

Access devices, such as catheters, are subject to causing infection and can have biofouling issues. Infection and intervention rates on access catheters can vary based upon the type of catheter and duration of placement. Infection of long-term blood access devices in particular can be associated with blood stream infections that can lead to patient death. Interventions designed to rescue an access from removal due to clotting or biofouling often requires that the patient undergo a revision treatment where the access device is removed and replaced. In some cases, it is necessary to sacrifice the compromised access location and place the device in a secondary location in the patient. Extending the patency of access devices can improve the viability of long-term placement and reduce the need for subjecting patients to the expense and trauma of unnecessary additional intervention procedures.

DETAILED DESCRIPTION

Figure 1:
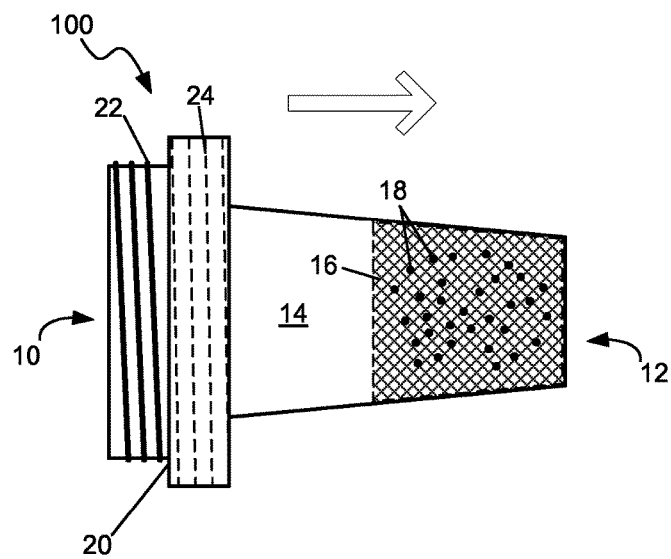
FIG. 1 is a schematic diagram of an insert in accordance with examples of the present disclosure.

Reference will now be made to the examples illustrated, and specific language will be used herein to describe the same. Features and advantages of the technology will be apparent from the detailed description which follows, taken in conjunction with the accompanying drawings, which together illustrate, by way of example, features of the technology.

It is to be noted that, as used in this specification and the appended claims, the singular forms "a," "an," and "the" include plural referents unless the context clearly dictates otherwise.

As used herein, the term "about" is used to provide flexibility to a numerical range endpoint by providing that a given value may be "a little above" or "a little below" the endpoint. The degree of flexibility of this term can be dictated by the particular variable and would be within the knowledge of those skilled in the art to determine based on experience and the description herein.

The term "catheter" is used herein to refer generally to devices used to provide fluid access to internal body spaces of a subject. This includes transcutaneous access as well as access through ducts, tracts, or passages of the subject's body. These access devices include, without limitation, vascular catheters, venous catheters, arterial catheters, feeding tubes, injection ports, perfusion ports, urinary catheters, ventricular shunt ports, and the like. Many different types of valves, fittings, junctions, connectors, chambers, syringes, or the like may be attached to the catheter, and thus, a "catheter system" includes any system with a catheter tube connected to or connectable to another structure, whether that other structure is a fluid delivery device (e.g., syringe, bag, or other dosing device), a connector fitting, a valve, insert in accordance with examples or the present disclosure (e.g., connector insert, syringe insert, secondary chamber insert, etc.), or the like.

The terms "connector," "fitting," "luer-type connector" or the like refer to the connection portion of two or more volumes at the location where they are joined together. For example, one type of connector is commonly referred to as a luer connector or a luer fitting. These connectors typically include female luer fitting and a male luer fitting, e.g., female luer fitting at the end or along a catheter tube and a male luer nozzle at the end or along a fluid delivery or extraction device (or vice versa). The female and male portion together comprise the "connector" or "fitting," whether part of the catheter tube or part of the fluid delivery or extraction device. The term "luer-type" connector should not infer this one type of connector, and thus includes both traditional luer connectors as well as other connector configurations that may be useful, including barbed connectors, pressure fit connectors, threaded connectors, etc. In some examples, the connector need not be for a catheter, but can be for a fluid directing device, e.g., needle, tube, etc., that is used to supply fluid to a container or substrate.

The term "active agent" is used to refer to pharmaceutically active agent(s), chemotherapeutic agents, or agents that promote, improve, or extend the viability of catheters, particularly by acting in the lumen of the catheter to prevent, retard, or ameliorate processes that compromise access or threaten patient health. Such processes include, without limitation, pathogenic invasion and infection, blood clotting, plaque buildup, and fungal growth. Active agents can also, in some applications, include drugs, such as chemotherapeutic agents or other pharmaceutical agents.

The term "cartridge" is used to describe the active agent retaining and releasing material, e.g., ceramic material, sponge, or other polymeric or porous or fibrous material, etc., that is used to hold the active agent and release the active agent when a fluid is flowed along or therethrough during use, regardless of the configuration of the structure. The cartridge is typically loaded with active agent in a position along a fluid pathway within an insert and in line with a fluid pathway of a catheter system as a whole.

The term "insert" includes any structure that can be placed in line along the flow path of a catheter system and contains or supports the cartridge. In one example, an insert can be within or partially within a connector of a catheter system, e.g., luer connector, syringe connector, barbed connector, threaded connector, etc., but it is noted that the insert can also be immediately adjacent to the connector or merely in line and part of a fluid flow path of a catheter system as a whole. For example, a syringe that includes a cartridge within the barrel of the syringe (but not within the connector of the syringe) would still be considered an insert because the syringe housing supports or holds the cartridge and the syringe housing is adapted to be inserted into the fluid pathway of a catheter system via a connector. Likewise, a chamber containing a cartridge that is outside of a connector is also considered an insert if it is connectable along a fluid pathway of a catheter system. In another example, a device that resides within (which includes wholly within or partially within) a catheter or other connector of a catheter system is also considered to be an insert. In other words, any structure that contains and/or supports a cartridge (typically loaded with an active agent) and is or can be attached via a connection to a catheter or other device in a catheter system is considered an insert.

Sizes, amounts, and other numerical data may be expressed or presented herein in a range format. It is to be understood that such a range format is used merely for convenience and brevity and thus should be interpreted flexibly to include not only the numerical values explicitly recited as the limits of the range, but also to include all the individual numerical values or sub-ranges encompassed within that range as if each numerical value and sub-range is explicitly recited. As an illustration, a numerical range of "about 1.0 to 2.0 percent" should be interpreted to include not only the explicitly recited values of about 1.0 percent to about 2.0 percent, but also include individual values and sub-ranges within the indicated range. Thus, included in this numerical range are individual values such as 1.1, 1.3, 1.5, and sub-ranges such as from 1.3 to 1.7, 1.0 to 1.5, and from 1.4 to 1.9, etc. This same principle applies to ranges reciting only one numerical value. Furthermore, such an interpretation should apply regardless of the breadth of the range or the characteristics being described.

As used herein, a plurality of items, structural elements, compositional elements, and/or materials may be presented in a common list for convenience. However, these lists should be construed as though each member of the list is individually identified as a separate and unique member. Thus, no individual member of such list should be construed as a de facto equivalent of any other member of the same list solely based on their presentation in a common group without indications to the contrary.

The present disclosure is directed to methods and devices for releasing active agent from a cartridge disposed within a catheter system. In one example, an insert for a catheter system can comprise an insert housing which defines a portion of a fluid pathway of the catheter system, a cartridge positioned within the insert housing in a manner to allow fluid flow along the fluid pathway such that fluid contacts the cartridge during the fluid flow, and an active agent associated with the cartridge. The active agent and the cartridge can be adapted to release active agent from the cartridge during the fluid flow.

In another example, a catheter system can comprise an insert including an insert housing which defines a portion of a fluid pathway of the catheter system, a cartridge positioned within the insert housing in a manner to allow fluid flow along the fluid pathway such that fluid contacts the cartridge during the fluid flow, and an active agent associated with the cartridge. Again, the active agent and the cartridge can be adapted to release active agent from the cartridge during the fluid flow. The system can also include a valve in fluid communication with the insert. Thus, the insert can be positioned with respect to the valve to reduce a concentration of infectious pathogens of being introduced from the valve into a catheter tube downstream from the valve. In this example, the valve can be any valve used in the medical field, including various 2-way valves, 3-way valves, stopcock valves, etc. Furthermore, it is noted that the insert can be positioned immediately adjacent to the valve, upstream from the valve along the fluid pathway, downstream from the valve along the fluid pathway, or within or about (which includes partially within or about) a connector portion of the valve. The catheter system can also further include the catheter tube that is configured to enter the subject or patient.

In another example, a method of tuning the release of an active agent from a cartridge adapted for insertion into a catheter system can include the steps of establishing a desired release profile for an active agent to be delivered into a catheter; and disposing a cartridge having the active agent associated therewith into a fluid pathway of a catheter system. Thus, when an aqueous solution contacts and passes by or through the cartridge, the active agent is released from the cartridge at the desired release profile.

Regarding these apparatus and methods, there are various ways of loading active agent onto a cartridge, and several of these approaches are disclosed and described in U.S. Provisional Patent Application No. 61/928,378 filed on Jan. 16, 2014, as well as Patent Cooperation Treaty Application No. PCT/US15/11722, filed in the U.S. Receiving Office on Jan. 16, 2015, each of which are incorporated herein by reference. For example, a cartridge associated with the active agent can be adapted to include one or multiple of the following properties: i) the cartridge has a porosity configured to delay or modulate the release of the active agent; ii) the active agent is chemically modified to alter its solubility in a predetermined flushing or locking solution; iii) the active agent is lyophilized on or into a surface of the cartridge; iv) a coating layer is included on the cartridge that delays or modulates the release of the active agent from the cartridge; v) the active agent is absorbed beneath a surface of the cartridge; vi) the active agent can be drawn into the cartridge via negative pressure or vacuum; and vii) the active agent can be mixed at different ratios with one or more molecules to modulate release.

In each of these examples, the cartridge may or may not be positioned within a connector portion of the insert. For example, the cartridge may be positioned within the connector (wholly or partially), immediately adjacent to the connector but not within the connector, or upstream or downstream from the connector, each somewhere along the fluid pathway. Example inserts can include in line containers, syringes, connector inserts positionable between tubes or luer-type fittings, connector inserts, or the like.

In each of the insert examples, the insert can include a male end configured for insertion into a female luer fitting of a catheter, and a female end configured to receive a male luer nozzle of a fluid delivery device (or other combination of luer connector arrangements as designed within the catheter system as a whole). As defined herein, other luer-type connections can also additively or alternatively be used, which are not strictly luer connectors, but act to connect catheter system structures together, e.g., barbed connectors, threaded connectors, pressure fit connectors, etc. It is noted that the term "fluid delivery device" does not preclude fluid extraction, and should be interpreted broadly to include any fluid movement effectuated by the "fluid delivery device," whether injecting or withdrawing fluid. The insert can also provide a fluid pathway connecting the female end and the male end (or other connection system); thus, the cartridge is positioned such that the fluid pathway is fluidly coupled to the cartridge. In one example, the fluid pathway is primarily between the cartridge and an interior wall of any structure of the catheter system. In another example, the fluid pathway is primarily through the cartridge. Also, it is noted that certain device structures can be defined in various ways, depending on their use. For example, a syringe can be used as a fluid delivery device when the insert is separate structure relative to the syringe. Alternatively, in some examples, the syringe may be the insert and the fluid delivery device, such as in examples where the cartridge is housed as part of the syringe.

It is noted that when discussing the present methods and inserts, each of these discussions can be considered applicable to each of these embodiments, whether or not they are explicitly discussed in the context of that embodiment. Thus, for example, in discussing a method that utilizes a porosity for a cartridge for affecting the release profile of the active agent, such a porosity can also be used in a connection with the cartridges used in the inserts disclosed herein, and vice versa.

Furthermore, the mechanism of release of the active agent from the cartridge can vary from application to application. For example, the release profile may be an elution profile or curve where the active agent is separated from a material by elution as the aqueous solution is passed by or through the cartridge. However, in examples where there are coatings, the release profile may be the result of initially a mechanical protection by a sugar or other coating, followed by elution of the active agent from the cartridge. Thus, the term "release profile" is intended to include these or other design parameters, and is more related the actual release curve and/or timing that occurs based on a specific active agent/cartridge design.

Active agent concentrations for loading into the cartridge can vary greatly, depending on the cartridge material, how the active agent is associated with the cartridge, the desired concentration to be released into the catheter or subject, and many of the other concepts described herein. However, without being limiting, loading concentrations can typically range from 0.01 wt % solution to 20 wt % solution. Likewise, without limitation, CHG in particular can be loaded at solution concentrations ranging from 0.01 wt % to 5 wt %, from 0.05 wt % to 3 wt %, or from 0.1 wt % to 1 wt %, for example. There may be embodiments where loading concentrations outside of this range may be beneficial.

The cartridges taught herein and utilized in the disclosed methods can be associated with a variety of active agents. Non-limiting examples of active agents that can be associated with the cartridges can include antimicrobial agents, antiviral agents, antifungal agents, antithrombotic agent, chemotherapeutic agents, other pharmaceutical agents, or combinations thereof. As would be appreciated by one of ordinary skill in the art, the exact agent or agents selected for association with the cartridge can be correlated to the subject receiving the catheter or the nature of the treatment or use of the catheter. In one embodiment, the active agent can be an antimicrobial agent, an antiviral agent, an antifungal agent, an antithrombotic agent, or combinations thereof. In another embodiment, the active agent can be a pharmaceutical agent, chemotherapeutic agent, or combination thereof. Other agents can be included as active agents or in conjunction with others of the above listed active agents. Non-limiting examples of such agents could include agents that promote the function of an active agent, e.g. by providing appropriate tonicity, pH, and salinity.

The active agent can be included in any form that can be held in the cartridge material while being releasable when locking the catheter. These can include solid forms such as powders, granules, crystals, and the like that are held in pore spaces within the cartridge. In one example, a suitable solid active agent can be formulated to go into solution or suspension in the presence of a locking or flushing fluid (or even a delivery fluid in the case of delivering pharmaceutical or chemotherapeutic agents), such aqueous fluids that include a physiologically appropriate saline solution. In another example, the cartridge can be impregnated with an active agent in fluid form which then dries and adheres to the cartridge material. Infusion of the cartridge with an aqueous (locking, flushing, delivery) fluid then reconstitutes the active agent for delivery into or through the catheter. The physical state of the active agent can also be modified in order to provide the desired release profile from the cartridge. For example, in one aspect, the active agent can be prepared prior to association with the cartridge, and/or can be deposited as part of a lyophilization process, an adsorption process, or an absorption process where the active agent is associated with the cartridge. Regardless, the association of the active agent with the cartridge can be accomplished through any method known in the art. For example, the active agent can be impregnated, chemically bound, statically bound, adsorbed onto or absorbed into the cartridge, dried, lyophilized, or otherwise adhered onto a surface of the cartridge, or any combination of such known methods. The amount of active agent associated with a cartridge for the insert can vary depending on the nature of the active agent and the method used to associate the active agent with the cartridge.

To illustrate, in one specific example, it is understood that MRSA (methicillin resistant *staph aureus*) can typically be killed using at least about 0.5 mg/liter of chlorhexidine gluconate or chlorhexidine digluconate (CHG, chlorhexidine gluconate, and chlorhexidine digluconate can be used interchangeably) in solution, and in some situations, up to about 16 mg/liter can be used, depending on the application, e.g., from 0.0005 to 0.016 mg/ml in solution. Thus, by designing a device that provides and leaves a greater concentration of CHG in the lumen of the catheter than what is minimally needed to kill MRSA, this pathogen can be effectively killed in accordance with examples of the present disclosure. Additionally, it is noted that the active agent loaded cartridge can be made to be safe to humans because a concentration that may be useful for killing MRSA could still be at a low enough concentration once in the blood that it has no negative side effects in the human host. Furthermore, by utilizing the technology described herein related to tuning of the release of the active agent from the cartridge, the device can be designed so that a majority of the released active agent remains in the catheter upon flushing or locking of the catheter. Furthermore, regarding the active agent per se, though a brief example utilizing CHG has been described, it is understood that other active agents can be used to flush or lock catheters, including, without limitation, silver sulfadiazine, rifampicin, minocycline, chlorhexidine diacetate (CHA), or the like.

The active agents or the form of the active agent can be modified in order to alter or modify the release profile of the active agent from the cartridge. In one aspect, the active agent can be chemically modified to alter the solubility of the agent in an aqueous (locking, flushing, delivery, etc.) solution. The change in solubility of the active agent can shift the release of the active agent earlier or delay it later as compared to an unmodified release profile. In another embodiment, the active agent can be chemically modified to reduce the solubility of the active agent. In another example, solubilizing groups can be added to increase the solubility of the active agent and cause it to become soluble or release more quickly from the cartridge. Chemical modifications can be accomplished through the addition of any hydrophilic or hydrophobic components known in the art so long as the modification does not significantly impact the function of the active agent or make the active agent incompatible with use in catheters.

The release profile of the active agent from the cartridge can also be adapted for a specifically desired release profile through the modification of the cartridge itself. For example, in one embodiment, the cartridge can be modified such that at least a portion of the cartridge and/or the active agent associated with the cartridge is coated with a coating layer that delays the release of the active agent from the cartridge following exposure of the cartridge to an aqueous solution. Typically, the coating would be over a portion or all of the active agent, but there are some coatings that may provide enhanced or reduced attraction between the active agent and the coating (compared to the cartridge), and would likewise slow (or alternatively increase) the release of the active agent by virtue of the presence of an undercoating. Specific examples of such an undercoating would depend on the active agent and its affinity with the undercoating compared to its affinity to the uncoated cartridge. For example, an undercoating can be prepared that includes an amphipathic molecule, i.e. having one side of the molecule that is water soluble (hydrophilic) and the other side that is not very water soluble (hydrophobic), thus, providing a non-soluble side that can be attracted or attached to the cartridge while the chemistry of the active agent is bound to the hydrophilic side for modulated release, or vice versa. Other arrangements can also be implemented as would be appreciated by one skilled in the art after considering the present disclosure.

Regarding examples where an overcoating composition is used, the active agent can be associated with the cartridge and then coated with a coating layer that impedes contact between the active agent and the aqueous solution which passes through the catheter. Once the coating layer begins to dissolve, the active agent can be released more and more rapidly, for example. In this embodiment, the coating layer can be water soluble and the chemical nature of the coating layer composition as well as the thickness of the coating layer can be selected based on the desired release profile for the active agent.

Typically, the coating layer includes water soluble materials that can be solubilized when contacted by aqueous solutions that are passed through the catheter and along or through the cartridge. The exact solubility of the material of the coating layer can be varied depending on the desired release profile. A wide range of water soluble materials can be used in the coating layer including, but not limited to carbohydrates including sugars or sugar alcohols. Examples of sugars that could be used include sucrose, glucose, dextrose, maltose, fructose, and the like. Examples of sugar alcohols include sorbitol and maltitol or the like. Other coatings can include glycols such as polysorbates, (e.g., polysorbate 80 and other molecular weight forms of polyethylene glycol), water soluble polymers such as non-cross linked low molecular weight vinyl alcohols and polyurethanes, hydroxyethylcellulose, ethylcellulose polymers, ethylene vinyl acetates, polyvinyl pyrrolidones, or the like. Any combination of these materials or other materials that would be suitable for coating compositions can likewise be used. In one embodiment, the coating layer can include a carbohydrate or a sugar-based coating.

The release profile of the active agent from the cartridge can alternatively be altered by modifying the porosity of the cartridge. The porosity of the cartridge can be modified by altering the materials used to form the cartridge or by altering the manufacturing techniques of the cartridge. In one embodiment, the cartridge can be made from a ceramic material, sponge, or other polymeric or porous or fibrous material. Non-limiting examples of materials from which the cartridge can be formed can include ceramics, high-density polyethylene (e.g., 30-50 micron pores, 15-40 micron pores, etc.), cellulose fibers or other fiber materials, polyurethane, foams, and combinations thereof. The cartridge can have a bulk volume, as a measure of porosity, of about 10% to about 90%. In a more particular embodiment, the cartridge can have a bulk volume of about 25% to about 75%.

As alluded to previously, the release profile of the active agent from the cartridge can be varied by both modifications to the active agent as well as modifications to the cartridge itself. For example, in one embodiment, the porosity of the cartridge can be modified and the active agent can be lyophilized. In another embodiment, the active agent can be lyophilized on a surface of the cartridge and at least a portion of the cartridge can be coated with a coating layer that delays the release of the active agent from the cartridge following exposure of the cartridge to an aqueous solution. Regardless of the nature of the cartridge material or the active agent, one or more of the following can be true of the inserts of the present disclosure. First, optionally, the cartridge can include an axial channel extending axially therethrough, or the cartridge can be porous enough to allow fluid to flow there therethrough, for example. Additionally, or alternatively, the active agent, regardless of form, can be deposited on or absorbed within the cartridge.

In each of these examples where the cartridge and/or the active agent is modified to modulate, hasten (accelerate), or delay the release of the active agent from cartridge and into the catheter, the timing of release of the active agent from the cartridge can be measured with respect to the volume of fluid passed primarily through the cartridge. These measurement techniques are not included to describe how the devices and methods are to be used, but rather, to merely describe a simple technique to determine whether the device has a predetermined release profile under a given set of conditions. In other words, a device having the release profiles described below can be used with other fluid volumes, other catheter fluids, etc. In one example, a "desired release profile" may be measured such that at least 80 wt % of the active agent content associated with the cartridge is delivered from the cartridge within the first 20 wt % of a predetermined volume. In another example, the desired release profile may be such that less than 20 wt % of the active agent content associated with the cartridge is delivered from the cartridge within the first 80 wt % of a predetermined volume. In another example, the desired release profile may be such that at least 90 wt % of the active agent content associated with the cartridge is delivered from the cartridge based on a total volume representing a catheter luminal fixed volume downstream from the cartridge. In another example, the desired release profile may be such that a volume of a flush through a lumen is greater than a fixed volume of the lumen and at least 90% of the agent is released from the cartridge within the last 10% of the flush volume lumen. In another example, the desired release profile may be such that when 20 mL of the aqueous solution is passed along or through the cartridge within the lumen of a 10 French diameter catheter, no more than 5 wt % of the active agent is released in the first 18 mL of the aqueous solution. In another example, the desired release profile may be such that when 20 mL of the aqueous solution is passed along or through the cartridge within the lumen of a 10 French diameter catheter, no more than 5 wt % of the active agent is released in the first 15 mL of the aqueous solution. In another example, the desired release profile may be such that when 20 mL of the aqueous solution is passed along or through the cartridge within the lumen of a 10 French diameter catheter, no more than 10 wt % of the active agent is released in the first 15 mL of the aqueous solution. In another example, the desired release profile may be such that when 20 mL of the aqueous solution is passed along or through the cartridge within the lumen of a 10 French diameter catheter, no more than 5 wt % of the active agent is released in the first 2 mL of the aqueous solution. In another example, the desired release profile may be such that when 3.0 mL of the aqueous solution is passed along or through the cartridge within the lumen of a 10 French diameter catheter, at least 95 wt % of the active agent is released in the last 2 mL of the aqueous solution.

Notably, the 20 mL volume or the 3 mL volume above are provided merely as examples in determining release profiles as they relate to shifting release profile curves. Release profiles can be determined with this methodology, but can be used in virtually any size catheter. This is because there are many different catheter volumes as it relates to lumen diameter and catheter length. For example, a 10 French catheter may vary in length from about 15 cm to about 35 cm, or at lengths outside of this range. Thus, the design for a locking volume can be significantly different from catheter to catheter. With this in mind, what is notable is that when flushing a catheter with whatever volume is desired, a cartridge/insert can be configured so that 80%, 90%, 95%, or more of the active agent should be present in the lumen volume at the end of the flush, or in the case of locking, you may want 80%, 90%, 95%, or more of the active agent present at the beginning of the locking process. Thus, a practitioner may want 1 to 4 mL to be released at the end of a flush, or alternatively, may want 1 to 4 mL released at the beginning of a lock. Alternatively, a device could likewise be designed so that the release occurs throughout the locking or flushing with a more even release curve. With respect to a flush, by causing the active agent to be released at the end of the flush, the amount of active agent entering the human patient can be limited. Alternatively, by limiting solution passing over the cartridge during a lock, this can likewise limit undue exposure of the active to the patient when using agents designed to increase life or patency of the catheter.

The inserts disclosed herein can be configured for insertion into the access end of an access device, such as a catheter, so as to communicate with the lumen of the access device. The inserts can likewise be used in even more complex catheter systems as describe also herein. More particularly, the insert, in one example, may be designed to be interposed at a connection between the access device and a locking, flushing, or delivery fluid device, such as a needleless syringe or similar volume device. As described above, the insert can be further configured to hold an active agent in the cartridge and to provide a predetermined release profile of the agent into the lumen of the catheter when an aqueous fluid is passed alone or through the cartridge.

The features and function of the insert, cartridge, and related methods are described above and exemplary embodiments of various inserts are shown in the accompanying figures and descriptions, such as the example shown in FIG. 1. It should be noted that FIG. 1 and subsequent FIGS. are schematics illustrating structural features of the devices described, and are not intended to convey scale. Furthermore, the exemplified drawings are but limited set of examples of how the devices can be designed. Those skilled in the art can modify the structure shown after considering the present disclosure. With this in mind, in one embodiment, an insert 100 has a female end 10 and a male end 12 connected by a fluid pathway 14 extending through the insert. The fluid pathway represents a portion of a larger fluid pathway of a catheter system. The fluid pathway can be primarily around the insert in some examples (not shown) where a wall of the catheter or catheter connector co-defines the pathway. A cartridge 16 located in the fluid pathway is configured for admitting fluid flow, and also has an active agent 18 associated therewith which can be released when contacted by an aqueous solution that passes through the fluid pathway and through or along a surface of the cartridge. For example, in a process of locking a catheter, an aqueous fluid can be delivered into the lumen of the catheter through the insert, where the direction of flow is indicated in FIG. 1 by an arrow. The active agent, such as chlorhexidine gluconate (CHG), in the cartridge can be released into the locking fluid according to a predetermined release profile and can enter the catheter with the fluid.

To facilitate the connection of the insert in a luer connection, the male end of the insert is configured for insertion into a female luer fitting at the access end of a catheter. The female end of the insert can be configured to receive insertion of a male luer feature of a fluid delivery device, such as the nozzle of a syringe or tube. This male/female relationship with respect to the fluid delivery device and the catheter is fairly standard in the industry, but an alternative male/female relationship can likewise we be used without departing from the scope of the present disclosure. In an embodiment, the insert can further include features for participation in a luer-type connection.

Referring again to the example in FIG. 1, a threaded collar 20 concentrically situated on the insert 100 can include threading of a size and pitch to interact with luer-type features on the connected devices. One such feature typically associated with male components of luer-type connection is a locking collar that engages with flanges or other protuberances on a female component. As shown, the threaded collar can include external threading 22 facing the female end 10 of the insert and situated to facilitate coupling of the insert with a fluid delivery device. Imposition of the insert in a luer-type connection is further facilitated by internal threading 24 facing the male end 12 of the insert and configured to engage a flange on the female luer fitting of the catheter or other access device.

Figure 2A:
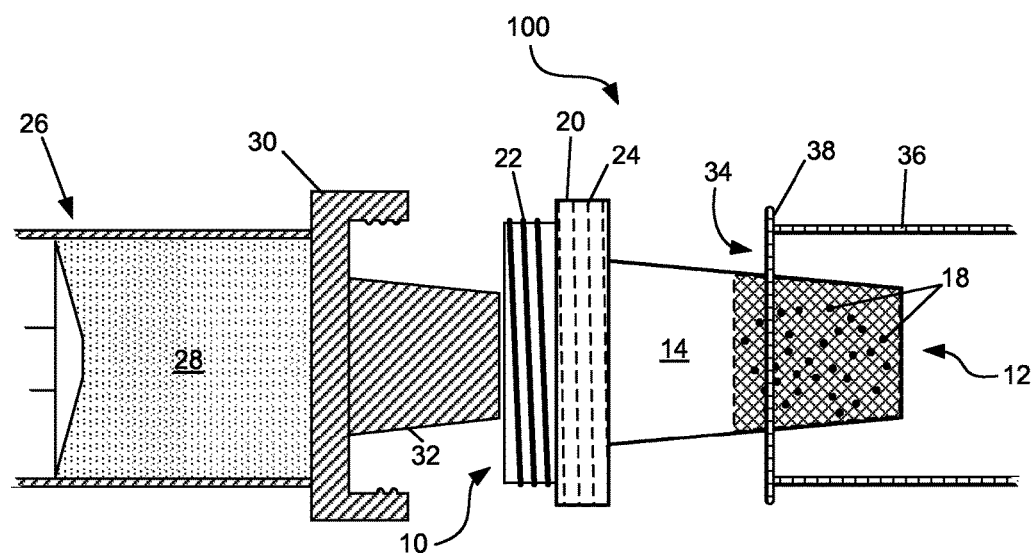
FIG. 2A is a schematic diagram of the insert of FIG. 1 prior to coupling with a syringe and a catheter fitting in accordance with examples of the present disclosure.
Figure 2B:
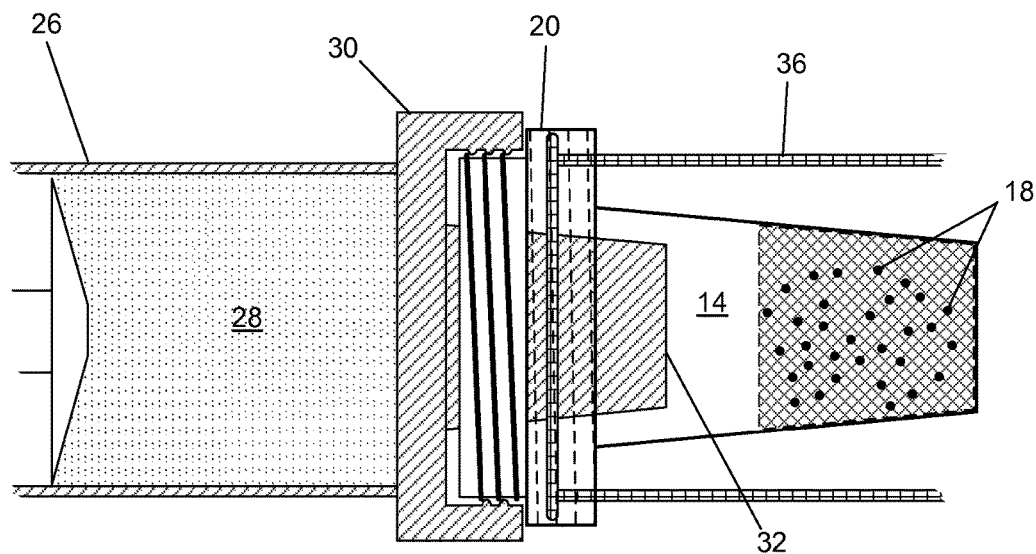
FIG. 2B is a schematic diagram of the insert of FIG. 1 after coupling with a syringe and a catheter fitting in accordance with examples of the present disclosure.

The action of the collar in connecting the insert 100 is illustrated by the example shown in FIGS. 2A and 2B, in which the fluid delivery device is a syringe 26 filled with a locking fluid 28. As mentioned, the fluid delivery device need not necessarily be a device for delivering fluid, as it could likewise be used for withdrawing fluid. The term "fluid delivery device" is used primarily for convenience in describing a typical delivery action, and thus, should not be considered limiting to delivery. Also noteworthy is that in this example, the syringe is a fluid delivery device. However, in other examples, hereinafter, the syringe can alternatively also act the insert (and the fluid delivery device), provided the cartridge is associated with the syringe (see FIGS. 7-9, for example), rather than a separate structure as is the case in FIGS. 2A and 2B. In this particular example, the syringe is inserted in the female end 10 of the insert, the spiral external threading 22 of the threaded collar 20 engages a locking collar 30 on the syringe. Screw coupling can be achieved by rotation of the syringe or insert until the syringe nozzle 32 is securely seated in the insert. A similar principle operates for the internal threading 24 facing the male end 12 of the insert. That is, when the male end of the insert is inserted into the female luer fitting 34 of a catheter 36, the flange 38 on the female luer fitting engages the internal threading so that relative rotation achieves coupling (a completed coupling is shown in FIG. 2B).

The fluid pathway inside the insert provides fluid communication with the lumen of the catheter and/or the lumen of a fluid delivery device. The dimensions of the fluid pathway from female end to male end can be selected to accommodate the luer fittings of the devices to be connected to the insert. In some cases, the dimensions of available fittings fall into one of a number of standard sizes. For example, International Organization for Standardization (ISO) specification 594 sets forth requirements for luer fittings for use with syringes and other medical transfusion apparatus. Under such standards, female fittings are larger than male fittings so as to provide an inner diameter that accommodates the outer diameter of the male fittings. One aspect of such fittings is a conical shape designed to provide a snug fit between components. As such, the lumens of such fittings typically exhibit a taper from a female end (if present) and/or toward a male end (if present). ISO-594 specifies a 6% taper. In an aspect, one or more of the dimensions of the insert are selected to conform to standard luer fittings. In one embodiment, the fluid pathway of the insert exhibits a taper extending from the female end toward the male end. In a specific embodiment the taper can be about 6%.

Referring again to FIG. 1, the insert 100 in this embodiment includes a cartridge 16 that is situated in the fluid pathway 14 and configured to admit fluid flow through the fluid pathway. As discussed above, the cartridge can be made of any material or have any configuration that is suitable for admitting fluid flow therethrough or there around, and further is adapted for holding active agent and then delivering the agent into the catheter lumen. The cartridge can be shaped and sized to fit inside the insert and remain in place during use. Where the cartridge is made of a resilient material, the cartridge can be sized and shaped so as to be held in place by expansive pressure. Alternatively, the cartridge may be small than the space that it is held, but the insert housing can be adapted to hold the cartridge in place appropriately as would be appreciated by one skilled in the art after considering the present disclosure. The cartridge can be secured in place by other means such as adhesive, protuberances on the inner surface of the insert, or by a mesh screen or cage, or by any other feature that does not preclude sufficient fluid flow and release of active agent.

Figure 3:
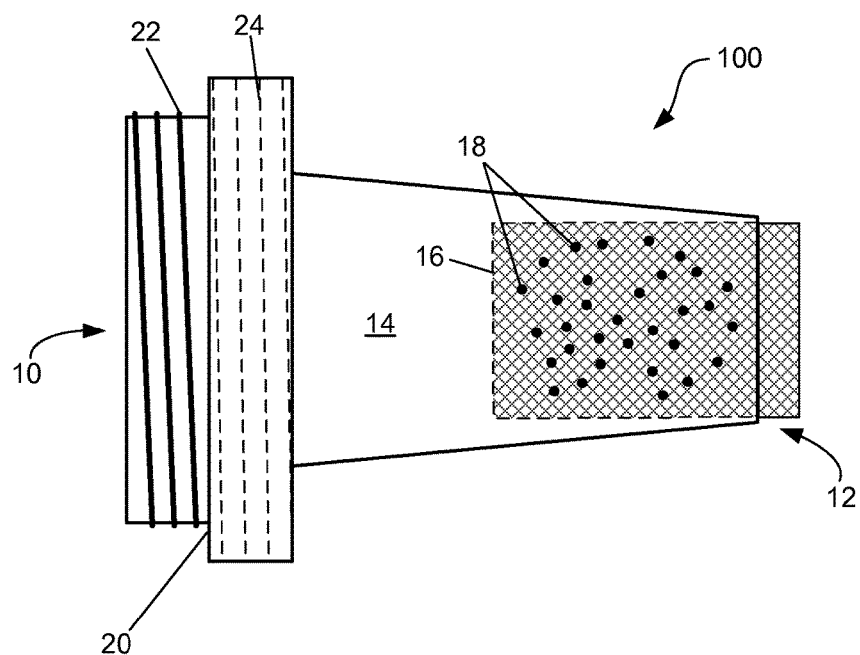
FIG. 3 is a schematic diagram of another insert in accordance with examples of the present disclosure.

The cartridge can be placed in any position relative to the ends of the insert. In a particular embodiment, the cartridge is placed in or adjacent to the male end. In one example, the cartridge is situated wholly within the insert as shown in FIG. 1. For some uses, effective locking may be realized by exposing a substantial portion of the cartridge to the lumen of the access device. Thus, the cartridge can be within the lumen of the connector (delivery device or catheter connector portion), within the delivery device, within the lumen of the catheter tube, or any combination of these locations. Accordingly, in another example of an insert 100 shown in FIG. 3, the cartridge 16 can extend past the male end 12 of the insert so that a portion of the cartridge extends into the lumen of the catheter when installed (but may still be considered to be inserted "into" the connector, i.e. inserted through the connector and structurally held in place by the connector). In one aspect, the male end of the insert serves to guide the cartridge into the female fitting of the access device and position the cartridge within the volume of locking fluid. In another aspect, a longer cartridge can be used so as to accommodate greater amounts of active agent. The size and shape of the cartridge can further be selected so as to leave an intervening space between the cartridge and the male fitting of a fluid delivery device coupled to the insert. This example is otherwise similar to that shown in FIG. 1, and includes a female end 10 and a male end 12 connected by a fluid pathway 14 extending through the insert. The cartridge is located in the fluid pathway is configured for admitting fluid flow, and also for retaining or holding the active agent 18 that is associated with the cartridge and then releasing the agent when an aqueous fluid is flowed through the fluid pathway. Again, a threaded collar 20 is concentrically situated on the insert and can include threading of a size and pitch to interact with luer-type features on the connected devices, and can include external threading 22 facing the female end of the insert and situated to facilitate coupling of the insert with a fluid delivery device. Also included is an internal threading 24 facing the male end 10 of the insert which is configured to engage a flange on the female luer fitting of the catheter or other access device.

Figure 4:
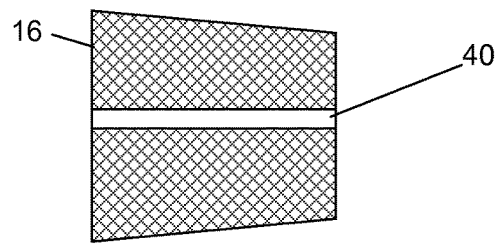
FIG. 4 is a cross-section diagram of a cartridge that is useable in an insert in accordance with examples of the present disclosure.

As disclosed above, in the cartridge of the insert can have channels or passages which pass primarily through the cartridge in order to facilitate flow of an aqueous fluid or liquid, and/or the cartridge can have a sufficient porosity to allow fluid flow therethrough. In a particular embodiment, an example of which is shown in FIG. 4, the cartridge can include an axial channel 40 extending axially therethrough. Such a channel 40 can serve to decrease resistance of a cartridge to the flow of fluid through the fluid pathway and thereby provide a desired effect to the release profile of the active agent from the cartridge. In a specific embodiment, the axial channel may coincide with the center axis of the cartridge as illustrated in FIG. 4. In another aspect, the channel can serve as an interface for diffusion of active agent into the fluid. It is noteworthy that while the active agent shown in the figures, such as FIG. 4 is shown being absorbed or impregnated into the cartridge material, in some embodiments, the active agent can be disposed substantially on the surfaces of the cartridge. Such surfaces can also include internal surfaces when porous materials are used. The cartridge of this FIG. is tapered similar to that of a luer connector; however, it is noted that any shape appropriate for a specific insert housing structure can be used. For example, the shape can be made to appropriately fit within the lumen of a syringe barrel, or a connector of a syringe, or a separate housing container designed specifically to contain the cartridges of the present disclosure. The cartridge may likewise be associated with a distal tip of a syringe plunger (the end that contacts the delivery fluid, for example).

Figure 5A:
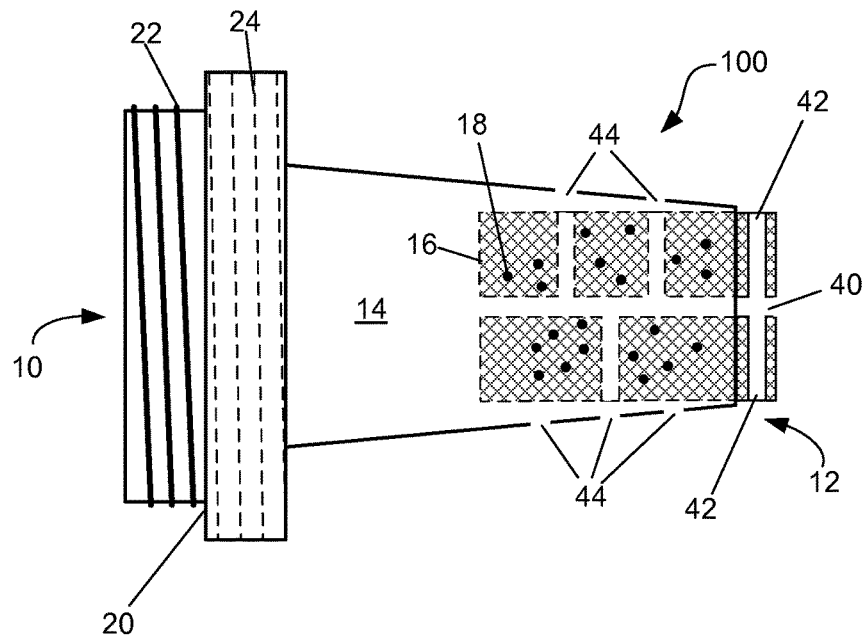
FIG. 5A is a schematic diagram of another insert in accordance with examples of the present disclosure.
Figure 5B:
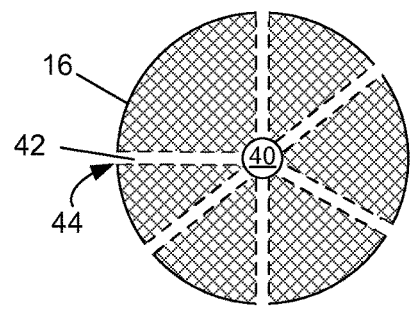
FIG. 5B is a cross-sectional diagram of a cartridge that is usable in an insert in accordance with examples of the present disclosure.

In a further embodiment, the axial channel can communicate with the circumference of the cartridge via one or more radial channels 42 as shown in FIGS. 5A and 5B. As shown in FIG. 5A, the radial channels can be located at any point along the length of the axial channel, and can join the axial channel either singly or in groups. In a particular aspect, the radial channels extend perpendicularly with respect to the axial channel. In another aspect, as the cross-section of a cartridge shows in FIG. 5B the radial channels can radiate from the axial channel at a plurality of angles with respect to the central axis of the cartridge. By providing additional paths for fluid to flow primarily through the cartridge, the radial channels can further decrease resistance and enhance the rate of flow through the insert. In another aspect, the radial channels can aid in distribution of the fluid. Where the cartridge extends past the male end 12, radial channels in the exposed portion of the cartridge can help to redistribute and backfill the infused fluid into the more proximal portions of the access device lumen.

Another feature for enhancing fluid flow can comprise one or more holes 44 penetrating the insert to provide fluid communication with the fluid pathway 14 and/or to expose portions of the cartridge to the lumen of the access device. In this aspect, holes can be included in conjunction with cartridges having channels as well as cartridges without channels. As shown in FIG. 5A, holes can be located adjacent a portion of the cartridge, providing an additional pathway for fluid within the cartridge to exit the insert. As also illustrated in FIG. 5A and also FIG. 5B, for inserts that include radial channels the holes can be positioned in correspondence with radial channels to complete communication between the axial channel and the lumen of an access device. In FIGS. 5a and 5b, other numerical references shown but not specifically discussed are similar to those described with respect to FIGS. 3 and 4.

Figure 6:
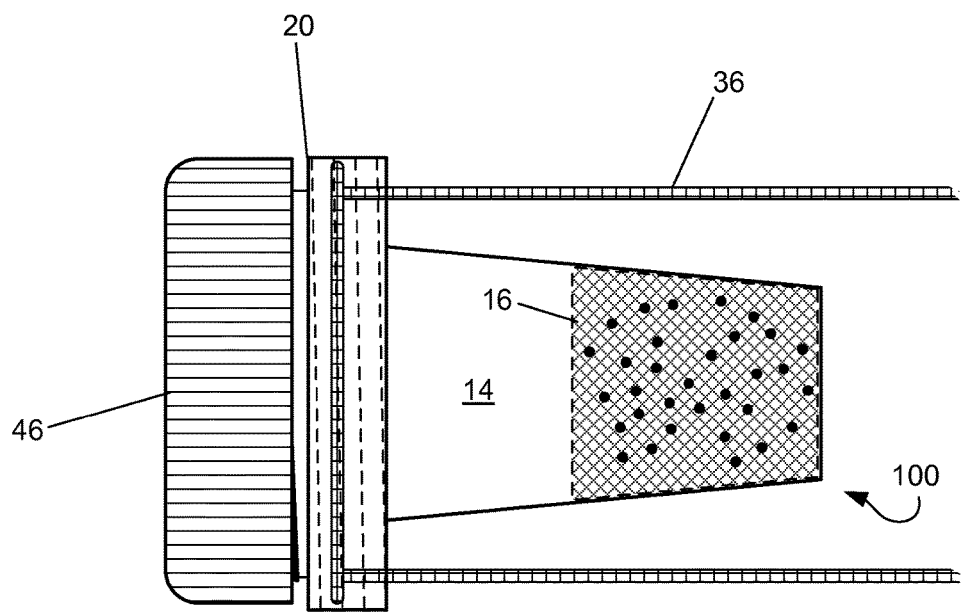
FIG. 6 is a schematic diagram of a capped insert coupled to a catheter in accordance with examples of the present disclosure.

As shown in FIG. 6, the insert 100 can include an end cap 46 that can be removably attached to the female end of the insert. The end cap can serve as a barrier to seal the insert (and therefore the catheter 36) from access. Some access placements call for injectable end caps that can be penetrated by a needle and then self-seal. In a particular embodiment, the insert includes a self-sealing injectable end cap for this mode of use. Again, as shown is the cartridge 16, fluid pathway 14, and threaded collar 20.

Figure 7:
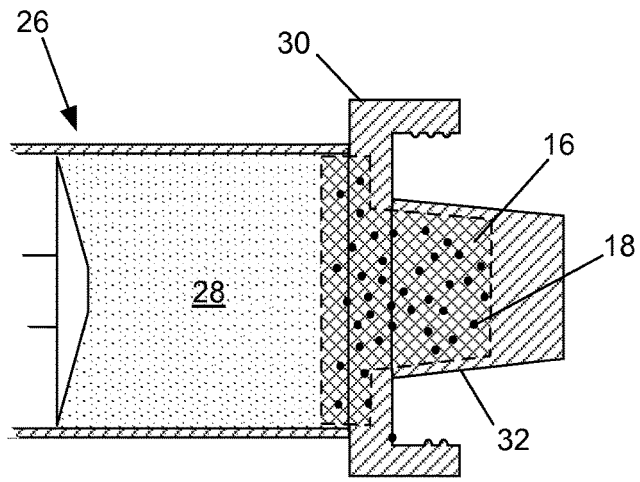
FIG. 7 is a schematic diagram of an insert in the form of a cartridge positioned within a connector of a syringe in accordance with examples of the present disclosure.
Figure 8:
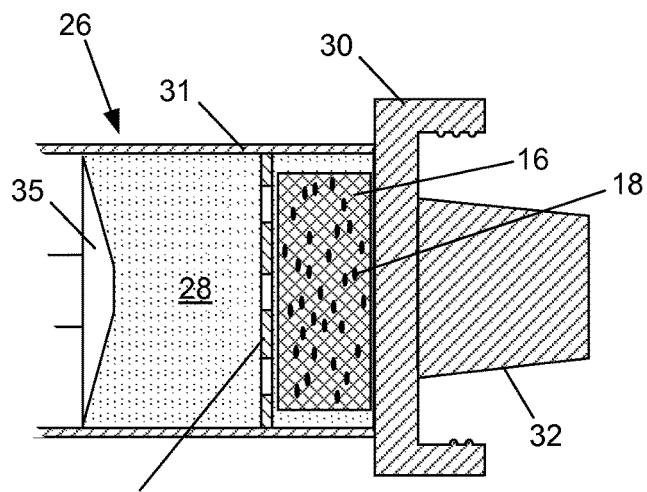
FIG. 8 is a schematic diagram of an insert in the form of a cartridge inserted just outside of and adjacent to a connector of a syringe in accordance with examples of the present disclosure.
Figure 9:
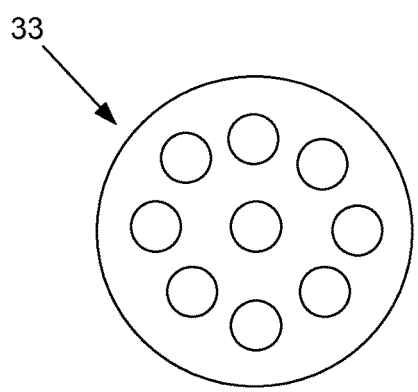
FIG. 9 is a top view of a channeled wall introduced in FIG. 8 in accordance with examples of the present disclosure.

FIGS. 7 and 8 depict an example where the insert is in the form of a syringe 26, which can be filled with locking or other delivery fluid 28. As shown in FIG. 7, a cartridge 16 loaded with active agent 18 is (partially) present within the connector, which in this case includes a locking collar 30 and a syringe nozzle 32. It is noted that in this embodiment, that the cartridge is pressure fit or otherwise integrated within the syringe, and thus, the cartridge can be highly porous to allow the fluid to flow therethrough. Alternatively or additionally, the cartridge can include channels therein to allow the fluid to flow therethrough. Other arrangements can likewise be prepared, as described elsewhere herein.

In FIG. 8, on the other hand, a different embodiment is shown where the cartridge is located adjacent to the connector portion or locking collar 30, but is wholly within a barrel 31 of the syringe (just outside of the connector portion). In this example, the cartridge is free-floating so that there is room around the perimeter for fluid to flow. To prevent unwanted movement of the cartridge and/or to keep the cartridge near the exit port or nozzle 32 of the syringe, a cage or channeled wall 33, shown from a top perspective in FIG. 9, can be integrated with the syringe. That being stated, there is no requirement that the cartridge be included at this location within the syringe, as it can be free floating without a channeled wall in some examples (sized to stay within the syringe and not block fluid flow when fluid is pushed through the nozzle), or the cartridge can even be attached or otherwise associated with the plunger 35. Any of these or other arrangements as describe herein or similarly configured can be used.

Figures 10A, 10B:
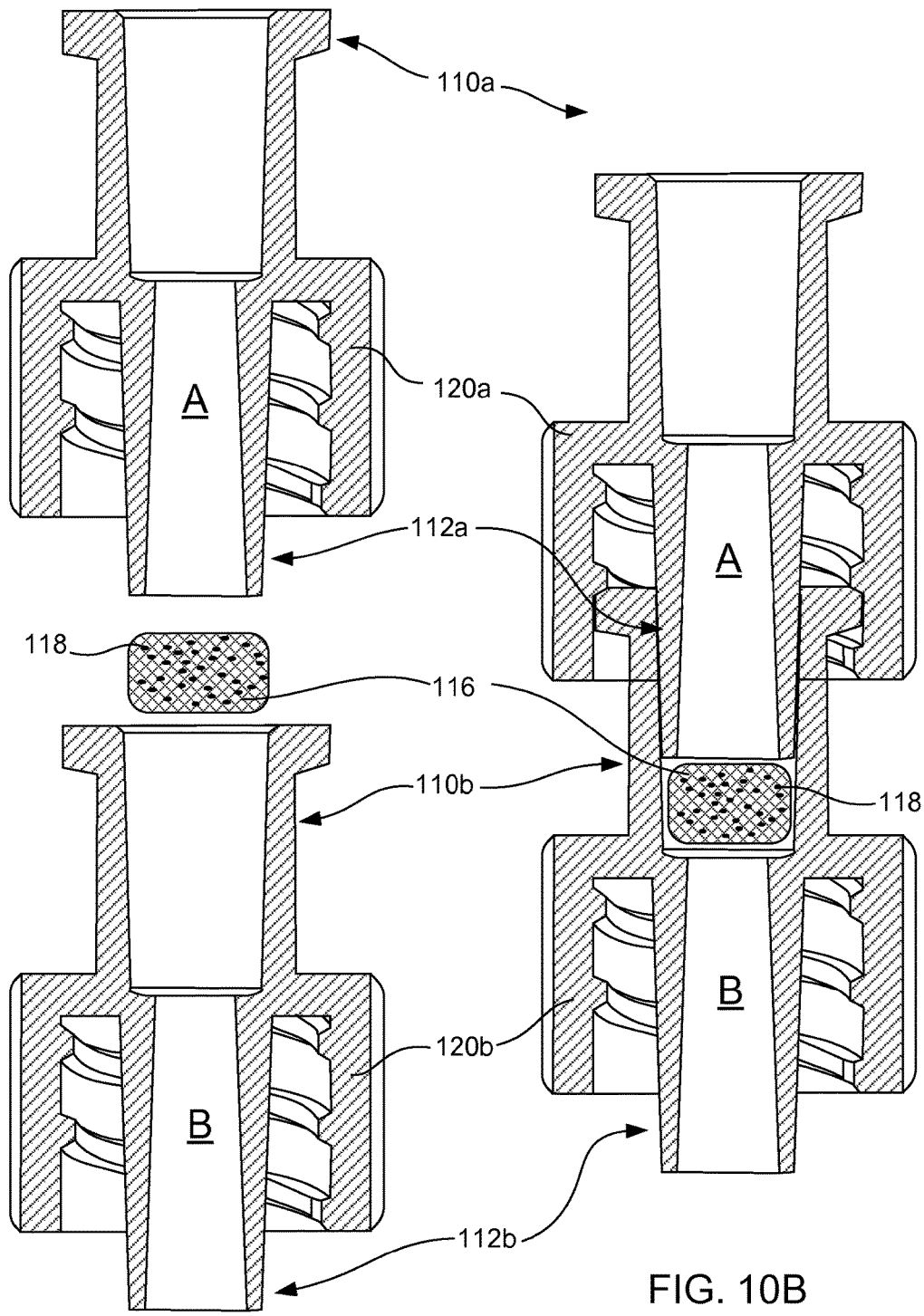
FIGS. 10A-10B are cross-sectional views of an insert in the form of two luer connector devices as connected together leaving a luminal space there between sufficient for insertion a cartridge in accordance with examples of the present disclosure.

FIGS. 10A and 10B provide cross-sectional views of another embodiment of the present disclosure. In this example, a pair of luer-type connectors (in this case, they are in fact luer connectors) are shown. Specifically, FIG. 10A shows the pair of connectors (Connector A and Connector B) prior to assembly, and FIG. 10B shows the pair of connectors after assembly. Each connector includes a female end 110a, 110b, a male end 112a, 112b, and a threaded collar 120a, 120b about the male end. A cartridge 116 is shown which contains an active agent 118, and is positioned between a space between Connector A and Connector B when the respective connectors are threaded together. Thus, the pair of luer-type connectors comprise the insert in this example, and can be placed between a fluid delivery device upstream (not shown) and/or other device, and a catheter connector downstream (not shown) or other device. For reference, "upstream" is a location within a fluid delivery device or catheter that is more distal to a patient, and "downstream" is a location that is more proximate to a patient. That being said, upstream and downstream are used for convenience to describe physical locations, but it is understood that these devices may have reversible fluid flow along the fluid pathway.

Figures 11, 12, 13:
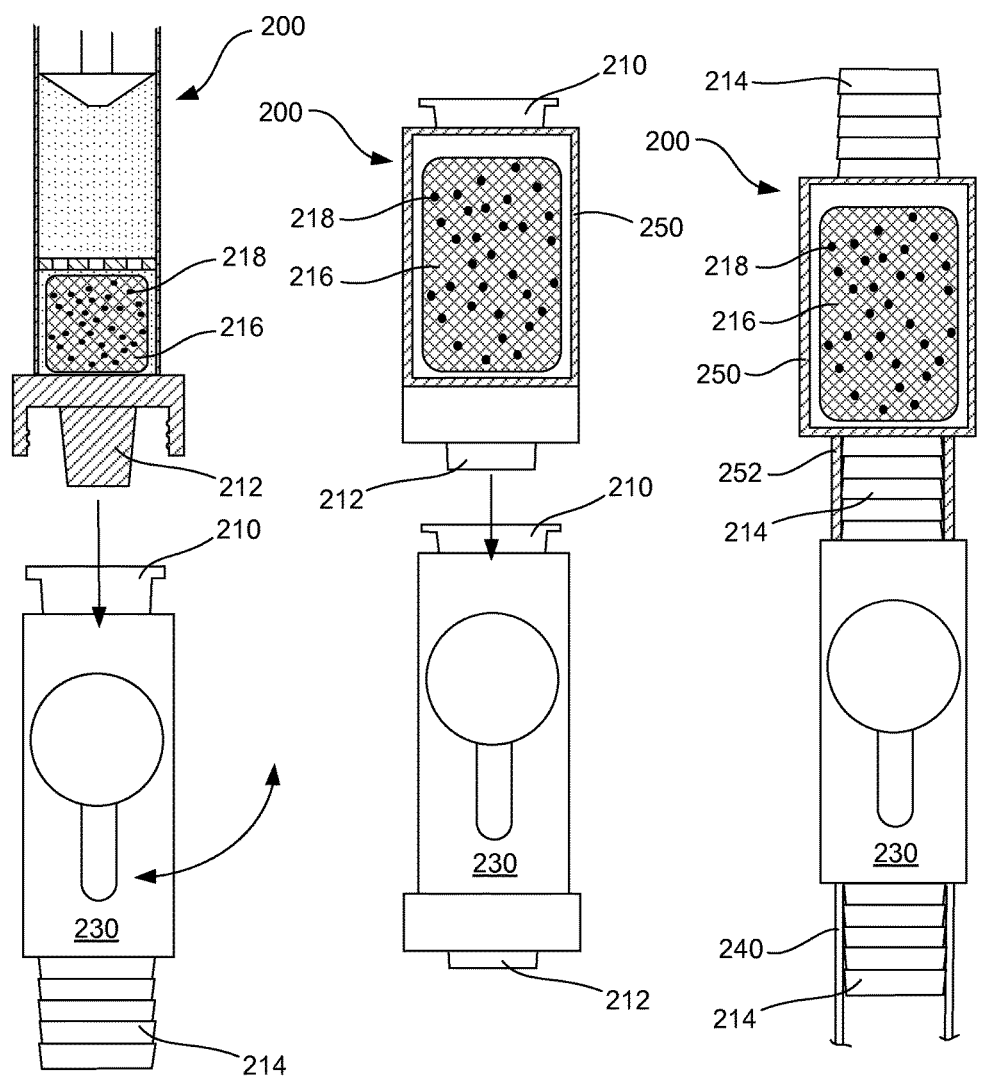
FIG. 11 is a schematic representation of a valve or stopcock interfacing via a luer connection with an insert in the form of a syringe containing a cartridge in accordance with examples of the present disclosure.
FIG. 12 is a schematic representation of a valve or stopcock interfacing via a luer connection with an insert in the form of secondary chamber containing a cartridge in accordance with examples of the present disclosure.
FIG. 13 is a schematic representation of a valve or stopcock interfacing via a barbed fitting with an insert in the form of a secondary chamber containing a cartridge in accordance with examples of the present disclosure.

FIGS. 11-13 show three separate example embodiments where an insert 200 of the present disclosure is interfaced with an ancillary device, such as a valve 230, to form a catheter system, or a portion of a catheter system. Shown in these FIGS., is a 2-way stopcock valve in particular, though other valves could likewise be used, e.g., 3-way valves, etc. Any of a number of potential connectors are also shown, including female luer connectors 210 as shown in FIGS. 11 and 12, male luer connectors 212 as shown in FIGS. 11 and 12, and barbed connectors 214 as shown in FIGS. 11 and 13. Each catheter system includes a cartridge 216 that is associated with an active agent 218. In FIG. 11, the insert is a syringe (as previously described), and in FIGS. 12 and 13, the insert is a container 250 defining a chamber that is in line with and along the fluid pathway of the catheter system. FIG. 13 in particular shows the walls of a catheter 240 adapted to interface with a subject, such as a human medical patient, and also shows a female connector 252 adapted to receive the barbed connector of the valve. These connector arrangements are merely exemplary, as any number of connector arrangements can be used as would be appreciated by one skilled in the art after considering the present disclosure.

Figure 14A:
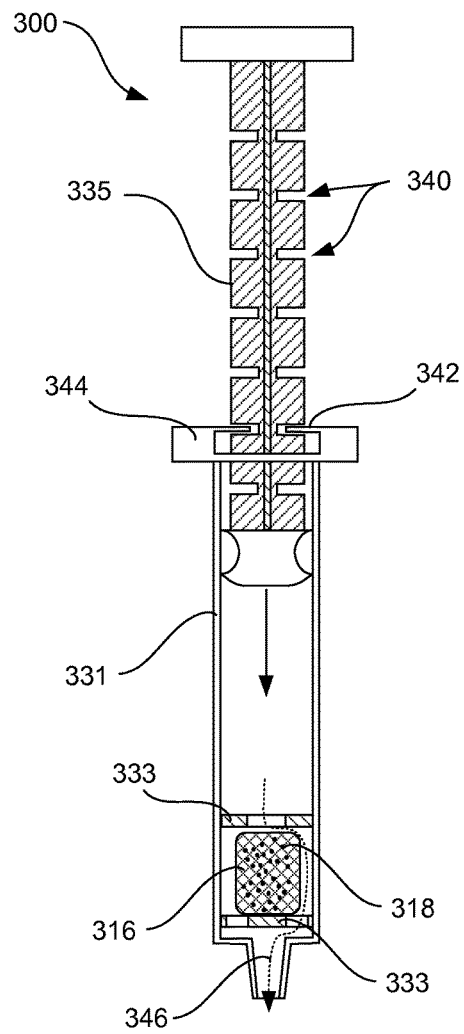
FIG. 14A is a schematic representation of an insert for a catheter system in the form of non-luer connection type syringe with a mechanical dosing plunger and containing a cartridge in accordance with examples of the present disclosure.

FIG. 14A depicts an alternative insert 300 in the form of a syringe that has a male a connector 312. This example shown is not a luer connector, but could be designed as a luer connector as well. In this example, the syringe includes a plunger 335 having a plurality of notches 340, and a barrel handle 344 having mechanical flaps 342 for catching the notches when the plunger is depressed into the barrel 331. Each notch may represent a specific volume of fluid, such as for example, 1 cc. This can allow for a more precise dosing with a mechanical feel. Also shown in FIG. 14A is a cartridge 316 with an active agent therein 318 similar to that shown and described in FIG. 8, but in this case, there are two cages or channeled walls 333 (one above and one below) to allow fluid flow through or around the cartridge, as shown by flow path 346. That being stated, there is no requirement that the cartridge be included at this location within the syringe, as it can be free floating without a channeled wall in some examples (sized to stay within the syringe and not block fluid flow when fluid is pushed through the nozzle), or the cartridge can even be attached or otherwise associated with the plunger. Any of these or other arrangements as describe herein or similarly configured can be used.

Figure 14B:
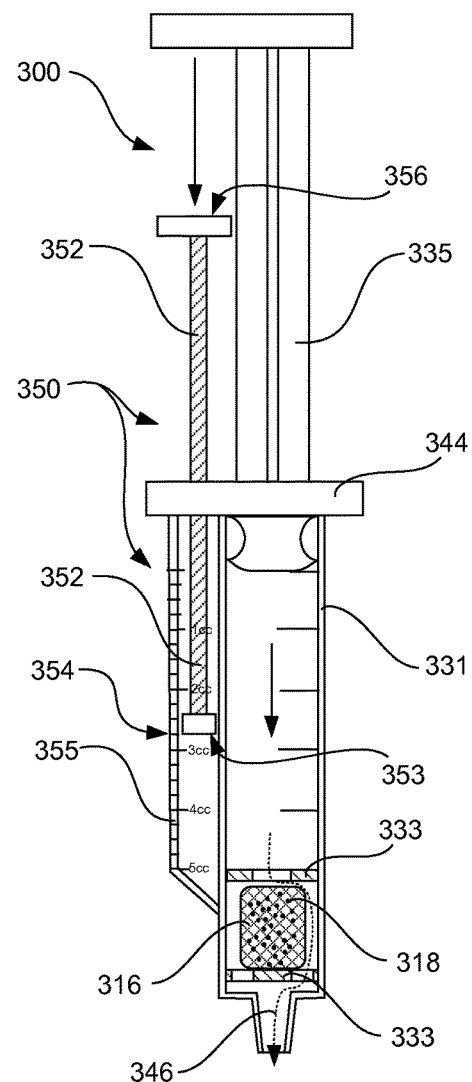
FIG. 14B is a schematic representation of an alternative insert for a catheter system in the form of non-luer connection type syringe with a mechanical auxiliary dosing mechanism and containing a cartridge in accordance with examples of the present disclosure.

FIG. 14B depicts yet another alternative insert 300 in the form of a syringe that has a male a connector 312. This example shown is not a luer connector, but could alternatively be designed as a luer connector. In this example, the syringe includes a plunger 335 and a barrel handle 344, but rather than mechanical flaps shown in FIG. 14A, this example has an auxiliary dosing mechanism, shown generally at 350, which acts to prevent the plunger from being depressed beyond a certain dosage limit dialed in by a stopper 352. Essentially, in this example, within or adjacent to the barrel handle is a mechanism that mechanically interfaces with the stopper, e.g., threaded interface, geared interface, teeth interface, ratchet interface, etc., so that the lower end 353 of the stopper can be dialed into a specific dosage by matching the lower end with a dosing line 354 marked on either a stopper guide 355, as shown, and/or immediately adjacent on the plunger. Thus, with the stopper positioned at the correct dosage line, the plunger can be freely pushed downward moving fluid therethrough only to be mechanically stopped by an upper portion 356 of the stopper. In this examples, a syringe that is completely filled with fluid is currently shown as being set for dispensing 2.75 cc of fluid, though any dosage could be delivered with this specific device ranging from 0 cc to 5 cc fluid (depending on where the stopper is set). This arrangement can allow for a more precise dosing with a mechanical safety mechanism in place. Also shown in FIG. 14B is a cartridge 316 with an active agent therein 318 similar to that shown and described in FIG. 8, but in this case, there are two cages or channeled walls 333 (one above and one below) to allow fluid flow through or around the cartridge, as shown by flow path 346.

That being stated, there is no requirement that the cartridge be included at this location within the syringe, as it can be free floating without a channeled wall in some examples (sized to stay within the syringe and not block fluid flow when fluid is pushed through the nozzle), or the cartridge can even be attached or otherwise associated with the plunger. Any of these or other arrangements as describe herein or similarly configured can be used.

It is noted that any of the device features shown in the FIGS., or described herein, can be combined together in any manner that is not specifically shown or described. For example, it is not the purpose of the present disclosure to put together every possible combination of features in the drawings.

Figure 15:
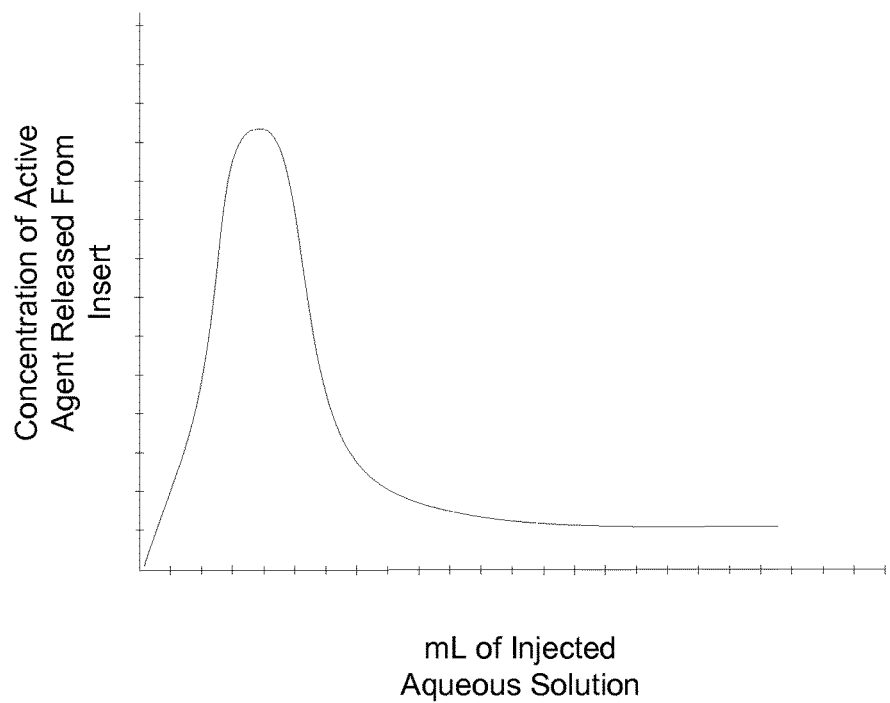
FIG. 15 is a plot of an exemplary release profile of an active agent in terms of concentration of active agents vs. the volume of aqueous solution injected through the catheter and insert in accordance with examples of the present disclosure.
Figure 16:
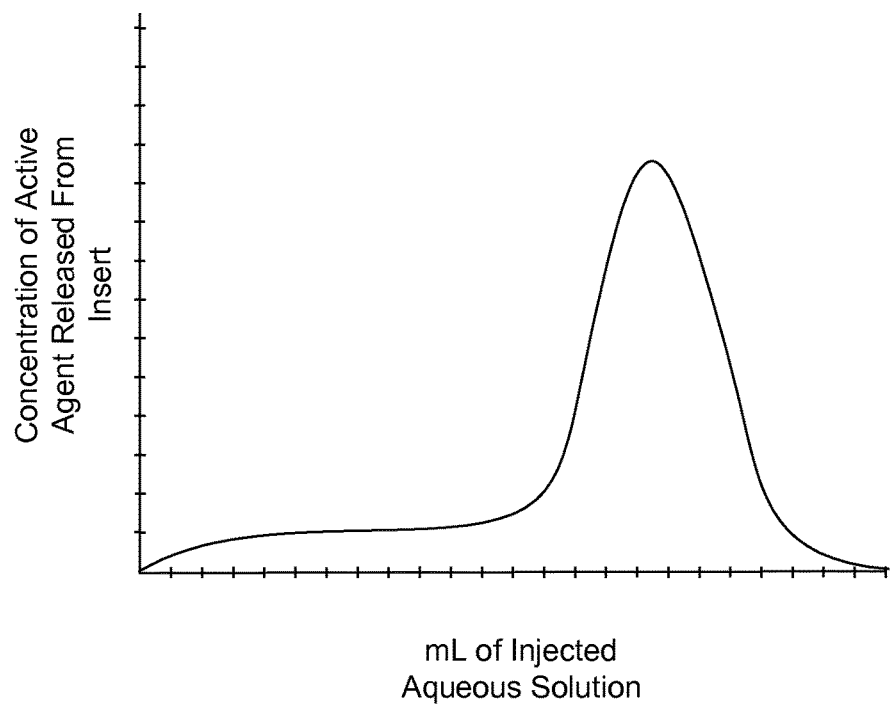
FIG. 16 is a plot of an additional exemplary release profile of an active agent in terms of concentration of active agent vs. the volume of aqueous solution injected through the catheter and insert in accordance with examples of the present disclosure.

Turning now to certain methods, the methods and inserts disclosed herein can provide a wide range of release profiles through the unique ability to tune the release of the active agent to a desired profile. In some situations, it may be desirable to have the active agent release very quickly following the passage of a portion of an aqueous solution. An example plot of a possible release profile of active agent that occurs substantially immediately following the contact of an aqueous solution is shown in FIG. 15. Techniques for hastening release as described herein can be used to generate a release curve similar to that shown in FIG. 15, or even a faster curve in some examples. In contrast, in some aspects it may be desirable to delay the release of the active agent until a substantial volume of the aqueous solution has passed over or through the insert and over or through the cartridge. FIG. 16 shows a plot of a possible release profile in which the highest concentration of active agent delayed until a certain volume of aqueous solution has passed through or over the insert and cartridge. Again, any of the techniques described herein to slow or delay release can be used. It is noted that units are not given for the curves shown in FIGS. 15 and 16 because they will be dependent on the design of the cartridge, the active agent used, the volume of aqueous solution to be flowed over the cartridge and through the catheter, etc. However, it is understood that the X-axis generally relates to fluid volume (e.g., 5 to 50 mL) and the Y-axis generally relates active agent concentration in the fluid within the catheter, which is active agent dependent.

In still another example, it may be desirable to modulate release. A wider more even release profile may be the desirable in some circumstances. While not expressly shown, it should be noted that the release peak of the profile of the active agent can be shifted forward and backward, or can be designed to modulate release with respect to the volume of aqueous solution passed over or through the insert and cartridge.

Example

Three sample cartridge materials were each loaded at three different loading concentrations of chlorhexidine gluconate (CHG) in solution (for a total of nine samples). The three cartridge materials selected were high density polyethylene 30-50 micron from Porex Corporation, high density polyethylene 15-40 micron from Porex Corporation, and cellulose fiber (0.4 g/mL density) from Porex Corporation. Three millimeter lengths of each was cut into three samples each, and each of the three samples was loaded with 0.01 wt % CHG, 0.1 wt % CHG, and 1 wt % CHG, respectively, with the balance being deionized water.

It is noted that higher active agent concentrations typically provide greater active agent concentrations within the lumen of the catheter upon flowing of a physiologic saline (or other appropriate fluid) across the cartridges. Porosity and/or density also impact the release rate of the active agent from the cartridge. Generally, lower porosity leads to higher concentrations being released more quickly for a given load density. Higher porosity generally leads to a more delayed release for a given load density. However, it is noted that other factors can also come into play that can impact the release profile, such as affinity between the active agent and the cartridge, whether there a coating or other chemical modification, lyophilization, etc.

While the forgoing example and description is illustrative of the principles of the present technology in one or more particular applications, it will be apparent to those of ordinary skill in the art that numerous modifications in form, usage and details of implementation can be made without the exercise of inventive faculty, and without departing from the principles and concepts of this technology. Accordingly, it is not intended that the technology be unduly limited.

What is claimed is:

1. An insert for a catheter system, comprising:
   an insert housing which defines a portion of a fluid pathway of the catheter system;
   a cartridge positioned within the insert housing in a manner to allow fluid flow along the fluid pathway such that fluid contacts the cartridge during the fluid flow; and
   an active agent associated with the cartridge, the active agent and the cartridge being adapted to release at least 80 wt % of the active agent from the cartridge during the fluid flow of a locking fluid, wherein the active agent comprises at least one of chlorhexidine gluconate, chlorhexidine digluconate, silver sulfadiazine, rifampicin, minocycline, or chlorhexidine diacetate.

2. The insert of claim 1, wherein the cartridge is not positioned within a connector portion of the insert.

3. The insert of claim 2, wherein the cartridge is positioned immediately adjacent to the connector portion of the insert.

4. The insert of claim 2, wherein the cartridge is positioned upstream from the connector portion of the insert along the fluid pathway.

5. The insert of claim 1, wherein the cartridge is positioned within a connector portion of the insert.

6. The insert of claim 5, wherein the cartridge is positioned only partially within the connector portion of the insert.

7. The insert of claim 1, wherein the insert comprises a syringe.

8. The insert of claim 7, wherein the cartridge is positioned within a barrel of the syringe, and not within a connector of the syringe.

9. The insert of claim 7, wherein the cartridge is positioned within a connector of the syringe.

10. The insert of claim 7, wherein the cartridge is associated with a plunger of the syringe.

11. The insert of claim 7, wherein a plunger of the syringe includes notches for providing mechanical dosing from the syringe and through the cartridge.

12. The insert of claim 7, further comprising an auxiliary dosing mechanism including a mechanical stopper operably associated with the plunger to provide a mechanical stop for the plunger and mechanical dosing from the syringe and through the cartridge.

13. The insert of claim 7, wherein the cartridge is adapted to be free floating within a barrel or connector of the syringe.

14. The insert of claim 7, wherein the cartridge is integrated with the syringe.

15. The insert of claim 1, wherein the insert comprises a pair of connectors joined together having the cartridge positioned within a space between the pair of connectors.

16. The insert of claim 1, wherein the active agent further includes an antimicrobial agent, an antiviral agent, an antifungal agent, an antithrombotic agent, or combinations thereof.

17. The insert of claim 1, wherein the active agent further includes a pharmaceutical agent.

18. The insert of claim 1, wherein the device has a release profile where at least 80 wt % of the active agent is delivered from the cartridge within the first 20 wt % of a volume of the locking fluid during use to lock a catheter.

19. The insert of claim 1, wherein the 80 wt % release of active agent is based on a 1 mL to 4 mL volume of locking fluid.

* * * * *